Figure 1:
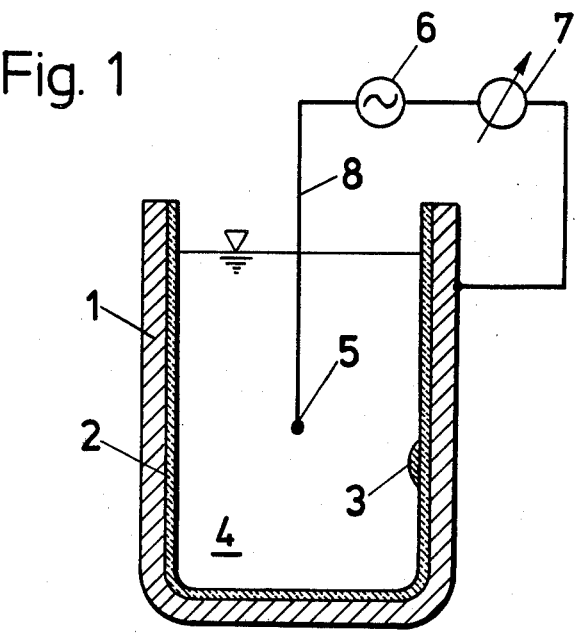

United States Patent [19]

Ehret

[11] 3,965,415

[45] June 22, 1976

[54] ALTERNATING VOLTAGE METHOD OF ELECTRICALLY DETECTING DAMAGE TO AN ENAMEL LAYER HAVING ONE OR MORE TANTALUM PLUGS

[75] Inventor: Rudolf Ehret, Schwetzingen, Germany

[73] Assignee: Pfaudler-Werke AG, Schwetzingen, Germany

[22] Filed: Mar. 24, 1975

[21] Appl. No.: 561,227

[30] Foreign Application Priority Data

Mar. 29, 1974 Germany............................ 2415317

[52] U.S. Cl. ................................................. 324/54
[51] Int. Cl.² ........................................ G01R 31/12
[58] Field of Search ...................... 324/54, 30 B, 29

[56] References Cited
UNITED STATES PATENTS

| | | | |
|---|---|---|---|
| 2,551,479 | 5/1951 | Wallace............................ | 324/30 B |
| 2,555,937 | 6/1951 | Rosenthal et al. ................ | 324/30 B |
| 2,651,751 | 9/1953 | Heath................................ | 324/30 B |
| 3,210,655 | 10/1965 | McGlasson et al. ................ | 324/54 |
| 3,555,414 | 1/1971 | Deichelmann........................ | 324/54 |
| 3,719,884 | 3/1973 | Laroche.............................. | 324/54 |
| 3,831,085 | 8/1974 | Kratavil .............................. | 324/54 |

*Primary Examiner*—Gerard R. Strecker
*Attorney, Agent, or Firm*—William R. Woodward

[57] ABSTRACT

A tantalum electrode is provided on a probe dipping into the electrically conducting contents of a reaction vessel of which the steel shell is protected by an enamel layer pierced by one or more protective tantalum plugs and an alternating voltage is applied between the tantalum electrode and the metallic shell of the reaction vessel. Both the electrode and the plug or plugs are provided with a passivating layer by the resulting alternating current and when these layers are formed the current stops except that it continues or starts again when there is a defect in the enamel layer. Very small currents can be used since the a-c component can be filtered and amplified for reliable detection.

1 Claim, 2 Drawing Figures

ALTERNATING VOLTAGE METHOD OF ELECTRICALLY DETECTING DAMAGE TO AN ENAMEL LAYER HAVING ONE OR MORE TANTALUM PLUGS

The invention relates to an improved method for electrical detection of faults in an anticorrosion enamel layer of a metallic apparatus such as a reaction vessel containing an electrically conducting medium, for example a conducting reaction mixture, during operation of the apparatus, and in particular for detecting faults in an apparatus in which one or more tantalum plugs have been provided either originally or in the course of repairs, for blocking faults in the enamel layer.

It is known from the disclosure of U.S. Pat. No. 3,555,414, which describes the provision of a tantalum screw to plug a fault in the enamel layer of a metallic reaction vessel, typically made of steel, to provide an electrode in contact with a conducting reaction mixture insulatedly mounted on a similarly enamelled probe structure extending into the mixture connected with a low-voltage direct current source and a relay external to the vessel for applying a direct current through the electrically conducting medium contained in the vessel, between the electrode and the metallic wall of the vessel, of such polarity as to produce a passivating layer on the tantalum plug or plugs provided in the vessel wall prior to utilizing the same voltage source for detecting the presence of any unplugged faults in the enamel layer.

Although the method just mentioned can be carried out successfully in practice under a variety of circumstances, there are certain limitations to its applicability with the common electrode materials because of corrosion by the contact with the contents of the reaction vessel, whereas if tantalum is resorted to as an electrode material for that method, the difficulty is encountered that the tantalum becomes embrittled by the absorption of hydrogen [see Corrosion Data Survey on Tantalum (Fansteel, May 8, 1972) Chapter VIII, Hydrogen Embrittlement of Tantalum, p. 123]. There is also an additional disadvantage in the method above described that particularly when the invariably small test voltages are used, extraneous electric fields are in a position to produce disturbances in the process.

It is accordingly an object of the present invention to improve the method above described and particularly to broaden its practical applicability, in such a way as to provide a still more reliable determination of damage to the enamel layer while at the same time avoiding corrosion effects or embrittlement of the electrode metal.

SUBJECT MATTER OF THE PRESENT INVENTION

Briefly, the electrode in contact with the electrically conducting contents of the apparatus is made of tantalum and the potential applied between the electrode and the metallic supporting structure or shell of the apparatus is a low-voltage alternating potential having a frequency suited for measurement of the resulting current flow without substantial interference from extraneous disturbing fields. The alternating voltage so applied first assures the coating of both the tantalum electrode and the tantalum plug or plugs of the enamel coating with a passivating layer. Thereafter, if there are no faults, the current in the circuit falls to a low value, and the presence of a fault can be detected by the presence of a value of current substantially in excess of that low value, the detection being done by measuring the current. The electrode with its passivating coating functions as a diode and conducts only in the direction of current for which no hydrogen is formed on the electrode and no embrittlement occurs. The diode so constituted also opposes the flow of current during those half cycles of the alternating potential in which current readily passes through the passivating layer of a conducting plug that may be provided in the apparatus in a position exposed to the contents thereof.

Where electrical disturbances to the measurement are produced chiefly by fields resulting from the utilization of electric power, the frequency used to detect faults in the enamel coating is chosen so as to avoid the electric power frequency and its lowest harmonics, but it is not necessary to avoid all harmonics of the power frequency and even a frequency such as four times the power frequency is usable.

With the improved process of the present invention there is accordingly no risk of embrittlement of a tantalum electrode, because in principle two tantalum rectifiers are present in the circuit, one the tantalum electrode provided in the conducting medium contained in the apparatus for purposes of fault detection and, second, the tantalum rectifier provided by the plug used either originally or by way of repair to remedy a fault in the enamel layer. When these diodes are formed by the provision of the passivating layer, no current can flow through the combination of them, but the occurrence of a fault in the enamel layer bridges one of these tantalum rectifiers with a short circuit and makes possible the flow of current. Currents that may be induced by disturbances can be reliably filtered out of the circuit if the frequency of the test potential is suitably chosen.

Figure 2:
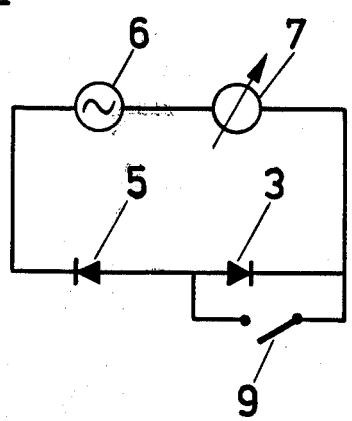

The invention will be further described by way of example with reference to the annexed drawing, in which:

FIG. 1 is a schematic representation of an apparatus for performing the method of the invention, and FIG. 2 is an equivalent circuit for the apparatus of FIG. 1.

As shown in FIG. 1, a steel container 1 made of a grade of steel suitable for enamel coating is provided with an anticorrosion enamel layer 2 on its inner surface. Faults found in the enamel coating upon manufacture or later during use are, if they occur, remedied by the provision of a tantalum screw 3 plugging the location of the fault and provided with a seal ring of polytetrafluoroethylene (not shown) sealing of the location of the fault. A tantalum electrode 5 in contact with an electrically conducting medium 4, typically a liquid medium, which may be a reaction mixture, is provided, for example at the lower end of a probe structure (not shown), which may be a closed steel tube provided with an enamel layer for protection against corrosion in the same way as the container 1, as more particularly shown in the abovementioned U.S. Pat. No. 3,555,414. In FIG. 1 there is shown just the electrode 5 and the conductor 8 connecting the electrode 5 to a circuit external to the container 1, but it is to be understood of course that, since it is desired to expose only the tantalum part of the circuit to the conducting medium 4, which may be very corrosive, the conducting lead 8 is suitably protected against contact with the medium 4 and, where the container 1 is a closed container, the connection 8 must also be insulated from the metallic structure of the container 1 and from a metallic structure used to support the electrode 5 inside the container, since such structure would normally be electrically at the same potential as the shell of the container.

In circuit with the electrode 5 and the steel shell of the container 1 are an alternating current source 6 and a current measuring device 7. The alternating current source 6 produces an alternating potential of about 5 volts or less which is applied between the electrode 5 and the container shell 1. The current measuring device 7 may be any appropriate kind of current detector or any well known kind of current meter, because by the measuring operation here involved is meant a magnitude determination that may determine only whether the current is or is not larger than a predetermined threshold value as well as the possibility of an indication of the actual value of the current. Thus a threshold switch or other detecting circuit may be used as well as a more versatile measuring device.

If the container 1 is used in the neighborhood of electrically powered machinery powered by alternating current at the usual power frequency of 60 Hz, a frequency of 200 Hz or 240 Hz may for example be selected for the frequency of the alternating current source 6, so that the test voltage can be reliably filtered and amplified by known means and thus separated and utilized without interference from power circuit disturbances. As is well known, synchronous detection circuits may also be used to provide the same effect as a sharp filter.

FIG. 2 is an equivalent circuit corresponding to the actual circuit of FIG. 1. In FIG. 2 the tantalum electrode 5 as well as the tantalum screw 3 are represented as rectifiers, corresponding to their mode of operation.

Since both the tantalum electrode 5 and the tantalum plug 3 are coated with a passivating layer, and it is more properly a passivating layer than an insulating layer, because it insulates essentially for only one direction of conduction, current flows in the circuit only when there is damage to the enamel layer, in which case the electrically conducting contents of the container come into contact with the metallic shell material of the container or of auxiliary portions of the apparatus, so that the tantalum screw 3 operating as a rectifier is short-circuited, as shown diagrammatically by the short-circuiting switch 9 in FIG. 2 which is shown in the open position or the condition in which no fault is present. Although in principle no current flows when no fault is present, there may be a small leakage current as a result of imperfections of insulation outside or inside the container without involving an actual fault in the enamel layer, so that the step of detecting the fault is more generally described as measuring the current, or determining the magnitude of a current, rather than detecting the presence of a current. Under many conditions, of course, there will indeed be no current except in the presence of a fault and the operation of detecting the fault may be more strictly a matter of detecting the presence of a current rather than, more broadly, measuring a current.

Although the current, in case of a fault, flows only in one direction, yet because the applied potential is alternating, the current will flow in pulses at the frequency of the potential, thus providing a signal with an alternating component at that frequency which can be filtered and amplified as aforesaid to isolate it and detect it free of interference from extraneous sources.

The passivating layer formed on the tantalum surfaces is sometimes described as an anodic oxide layer.

I claim:

1. Method of electrical detection of faults in an anti-corrosion enamel layer of a metallic structure of an apparatus containing an electrically conducting medium and provided with at least one tantalum plug, comprising:

providing an insulated tantalum electrode in said medium in electrical contact therewith together with connection means, insulated from said apparatus, for connecting said tantalum electrode to a potential source external to the portion of said apparatus containing said medium;

applying a low voltage alternating potential between said tantalum electrode and said metallic structure while said medium is contained in said apparatus both to assure the coating of said tantalum electrode and of said tantalum plug(s) with a passivating layer and to furnish current for detection of faults in said enamel layer, and measuring the current flow produced by said application of potential after said tantalum electrode and said tantalum plug(s) have been coated with said passivating layer, thereby to determine the presence of a fault in said enamel layer, the frequency of said alternating potential being chosen so as to favor measurement of said current flow without substantial interference from extraneous electric-current-inducing fields.

* * * * *